(12) United States Patent
Morales

(10) Patent No.: US 9,217,696 B2
(45) Date of Patent: Dec. 22, 2015

(54) ULTRA-RAPID DIAGNOSTIC TISSUE PREPARATION AS AN ALTERNATIVE TO FROZEN SECTION

(71) Applicant: THE UNIVERSITY OF MIAMI, Miami, FL (US)

(72) Inventor: Azorides Morales, Coral Gables, FL (US)

(73) Assignee: The University of Miami, Miami, FL (US)

( * ) Notice: Subject to any disclaimer, the term of this patent is extended or adjusted under 35 U.S.C. 154(b) by 0 days.

(21) Appl. No.: 14/348,304

(22) PCT Filed: Sep. 28, 2012

(86) PCT No.: PCT/US2012/057907
§ 371 (c)(1),
(2) Date: Mar. 28, 2014

(87) PCT Pub. No.: WO2013/049564
PCT Pub. Date: Apr. 4, 2013

(65) Prior Publication Data
US 2014/0234895 A1    Aug. 21, 2014

Related U.S. Application Data

(60) Provisional application No. 61/540,947, filed on Sep. 29, 2011.

(51) Int. Cl.
*A61B 10/00* (2006.01)
*G01N 1/31* (2006.01)
(Continued)

(52) U.S. Cl.
CPC .................. *G01N 1/312* (2013.01); *G01N 1/06* (2013.01); *G01N 1/30* (2013.01); *G01N 1/36* (2013.01)

(58) Field of Classification Search
CPC ........................................................ G01N 1/30
See application file for complete search history.

(56) References Cited

U.S. PATENT DOCUMENTS

| 6,207,408 B1 | 3/2001 | Essenfeld et al. |
| 6,586,713 B2 | 7/2003 | Essenfeld et al. |

(Continued)

FOREIGN PATENT DOCUMENTS

| WO | 01/44784 | 6/2001 |
| WO | WO-0144784 | 6/2001 |

(Continued)

OTHER PUBLICATIONS

University of Miami, et al., Australian Office Action mailed Sep. 30, 2014 for AU 2012315744, 5 pages.

(Continued)

*Primary Examiner* — Jyoti Nagpaul
(74) *Attorney, Agent, or Firm* — Blakely Sokoloff Taylor & Zafman LLP

(57) ABSTRACT

Improved methods and systems for processing of solid tissue are described. The method may be performed manually or automatically. The system may have modules such as (i) a grossing module where a fresh tissue is sliced to prepare a tissue specimen, (ii) a hardening module that hardens the tissue specimen, (iii) an impregnating module that impregnates the tissue specimen that was hardened, and (iv) an embedding module that embeds a tissue specimen that was hardened and impregnated. Fresh (i.e., not fixed or frozen) tissue, which was excised to diagnose disease or to assess surgical treatment, is grossed to about 0.6 mm. Preferably, the hardening of fresh tissue is initiated, but not completed, during grossing by contact with a chemical admixture. Preferably, dry ice, a thermoelectric device, or a gas condenser cools a metal mold containing the embedded specimen. It is sectioned and then microscopically examined as an alternative to histologic examination of a frozen section to avoid the known problems of discordant and deferred diagnosis.

31 Claims, 9 Drawing Sheets

(51) Int. Cl.
  *G01N 1/06* (2006.01)
  *G01N 1/36* (2006.01)
  *G01N 1/30* (2006.01)

(56) References Cited

U.S. PATENT DOCUMENTS

| | | |
|---|---|---|
| 6,793,890 B2 | 9/2004 | Morales et al. |
| 7,470,401 B2 | 12/2008 | Morales |
| 7,547,538 B2 | 6/2009 | Morales et al. |
| 8,221,996 B2 | 7/2012 | Morales et al. |
| 8,288,168 B2 | 10/2012 | Morales |
| 2001/0000487 A1 | 4/2001 | Essenfeld et al. |
| 2001/0043884 A1 | 11/2001 | Essenfeld et al. |
| 2001/0051365 A1* | 12/2001 | Morales et al. ............ 435/173.4 |
| 2004/0004075 A1 | 1/2004 | Morales et al. |
| 2005/0090017 A1 | 4/2005 | Morales |
| 2008/0153127 A1 | 6/2008 | Morales et al. |
| 2009/0136992 A1 | 5/2009 | Morales |
| 2011/0201115 A1 | 8/2011 | Pearlman et al. |

FOREIGN PATENT DOCUMENTS

| | | |
|---|---|---|
| WO | 2005/040763 | 5/2005 |
| WO | WO-2005040763 | 5/2005 |

OTHER PUBLICATIONS

Int'l Search Report for PCT/US2012/057907, all pages (Sep. 2012).
Written Opinion for PCT/US2012/057907, all pages (Sep. 2012).
Int'l Preliminary Report on Patentability for PCT/US2012/057907, nine pages (Apr. 2014).

* cited by examiner

ULTRA-RAPID DIAGNOSTIC TISSUE PREPARATION AS AN ALTERNATIVE TO FROZEN SECTION

CROSS-REFERENCE TO RELATED APPLICATIONS

This application is the U.S. national phase of International Application No. PCT/US2012/057907, filed Sep. 28, 2012; which designated the U.S. and claims benefit of U.S. Provisional Application No. 61/540,947, filed Sep. 29, 2011; the entire contents of each of which are hereby incorporated by reference.

FIELD OF THE INVENTION

The present invention relates to chemical processes and mechanical apparatuses for diagnostic tissue preparation. A fresh (i.e., not fixed or frozen) sample of solid tissue, which was excised from a patient's body in the course of surgery, can be prepared (i.e., grossed then processed) as an alternative to histologic examination of a frozen section and does not suffer from the latter's artifacts. These methods and these systems enable intraoperative diagnosis by histologic examination of a paraffin section that avoids artifacts encountered when a frozen section is examined.

BACKGROUND OF THE INVENTION

Methods and systems for tissue processing have been described (see WO 99/09390, WO 01/44783, WO 01/44784, and WO 2005/40763). They required a mixture of at least ketone and alcohol for chemical processing. Here, it is shown that alcohol is not required. A tissue sample can be obtained from a patient during surgery. A specimen thereof can be processed to a tissue block, the block is sectioned, and a tissue section is examined by an anatomic pathologist. Histologic examination of the tissue section and diagnosis are completed prior to the patient leaving surgery. An advantage of the invention over frozen sections is that the morphology of tissue sections viewed under the microscope is preserved in tissue blocks. The quality of sections from a tissue block appears to be the same whether the block was prepared by conventional processing or the invention. Discordant or deferred diagnosis, which is primarily due to artifacts observed during histologic examination of frozen sections, would be avoided by use of the present invention.

Intraoperative pathology consultation involves gross and microscopic examination of a sample obtained from a patient during surgery. Most often, histologic examination of a tissue section under the microscope is carried out by dye staining to examine histomorphology. This is conventionally performed on a "frozen" section from a solid tissue such that diagnosis by an anatomic pathologist is possible prior to the patient leaving surgery (i.e., intraoperatively). See Keeney & Leslie, JAMA 300:1074-1075 (2008). The history of Wilson's development of the frozen section technique was recounted at the centenary of its publication by Gal & Cagle, JAMA 294: 3135-3137 (2005) and Lechago, Arch, Pathol. Lab. Med. 129:1529-1530 (2005).

Laboratory accreditation by the College of American Pathologists (CAP) requires that intraoperative diagnosis using a frozen section be confirmed by later study of a so-called "permanent" section obtained from the same tissue, which was previously used to obtain the frozen section, embedded in a paraffin block. From the reports of participants in the CAP Q-track program, there was a discordance between frozen section and permanent section (i.e., an adequate frozen section study with an intraoperative diagnosis that has diagnostic disagreement with the paraffin section) of at least about 1%-2%. See Raab et al., Arch. Pathol. Lab. Med. 130:337-342 (2006). For this reason, as well as delay caused by deferred diagnosis, it would be desirable to provide intra-operative diagnosis of a section from a tissue block prepared by the present invention. But shortening the time required to prepare a tissue specimen for histologic examination from a surgical sample such that intraoperative diagnosis is possible has taken substantial modifications of existing methods and systems.

These improvements in methods and systems for tissue preparation are now described. They are characterized by (i) grossing solid tissue to a uniform thickness of about 0.6 mm and/or (ii) a chemical admixture of at least a ketone and an oil to harden a tissue specimen and/or (iii) a cooler to solidify a block containing a tissue specimen. Preferably, a tissue sample is first contacted with the chemical admixture during grossing to initiate hardening of the tissue and thereby facilitate its slicing into one or more tissue specimens. The lack of histologic artifacts is an improvement over conventional histologic examination of a frozen section that it is known in the art can be expected to produce discordant and deferred diagnoses. The requirement to perform a later study of a permanent section becomes moot because consistent morphology is obtained by the present invention.

Other advantages of the invention are discussed below or would be apparent to a person skilled in the art from that discussion.

SUMMARY OF THE INVENTION

It is an object of the invention to provide rapid diagnostic tissue preparation. A sample of solid tissue, which was excised from a patient's body during surgery, is processed as a tissue specimen without prior freezing. Tissue sections from a block of the processed specimen have morphologic characteristics of similar or identical quality as compared to a paraffin block prepared using conventional processing. This is an improvement over histologic examination of a frozen section, does not suffer from the morphologic artifacts of the latter, precludes the need to reprocess tissue, and avoids delay.

The methods and systems are compatible with processing of tissue specimens to produce a block that is sectioned for histology, in situ antibody binding, nucleic acid hybridization, other proteomic or genetic analyses (e.g., fingerprinting of fragments or determining their sequence), archival preservation of morphology and nucleic acids, and combinations thereof.

In a first embodiment, a method is provided comprising: (a) hardening a tissue specimen in a whispering gallery, wherein the specimen is contacted with a chemical admixture and microwave energy; (b) impregnating a tissue specimen under vacuum, wherein the specimen is contacted with a molten matrix and thermal energy; and (c) embedding a tissue specimen in a block and solidifying the block, wherein the solid block may be sectioned for histologic examination intraoperatively. It is preferred that a tissue sample obtained by surgery is grossed to a substantially uniform thickness (e.g., about 0.6 mm in the smallest dimension) in contact with a chemical admixture to initiate (but not complete) hardening. The tissue specimen may be about 0.1 mm or more, about 0.2 mm or more, about 0.3 mm or more, about 0.4 mm or more, or about 0.5 mm or more in thickness. The tissue specimen may be about 1 mm or less, about 0.8 mm or less, or about 0.7 mm or less in thickness.

In a second embodiment, a system is provided comprising: (a) a hardening module to harden a tissue specimen, (b) an impregnating module to impregnate a tissue specimen that was hardened, and (c) an embedding module to embed a tissue specimen that was hardened and impregnated in a solid block. A hardening module is comprised of (i) a first chamber having an interior shaped as a whispering gallery; (ii) a first lid that isolates the first chamber when closed, is opaque to microwave radiation, and accesses the first chamber when open; (iii) a first gasket retaining chemical fumes and evaporation within the interior of the first chamber; and (iv) a radiation source transmitting microwave energy to the interior of the first chamber. A tissue specimen is contacted with a chemical admixture in the first chamber. An impregnating module is comprised of (i) a second chamber having an interior capable of providing a reduced pressure relative to the exterior; (ii) a second lid that isolates the second chamber when closed and accesses the second chamber when open; (iii) a gasket maintaining a pressure differential between the interior and the exterior of the second chamber; (iv) a pump at least decreasing pressure within the interior of the second chamber below 1 bar; and (v) a heater conducting thermal energy to the interior of the second chamber. The hardened tissue specimen is contacted with a molten matrix in the second chamber. An embedding module is comprised of a cooler conducting thermal energy from a block in which a processed tissue specimen is embedded in matrix such that the matrix is solidified.

Optionally, a holder (e.g., cassette assembled from interlocking halves, the sides of which are perforated to permit solution exchange) may carry one or more tissue specimens of the same type within the first and the second modules, as well as therebetween. The holder may be disassembled, the processed tissue specimen may be removed from the holder then placed in the interior of an optional mold, and the tissue specimen may be embedded within the mold filled with molten matrix and covered by at least a part of the holder (e.g., one half having a label identifying the tissue specimen). It is preferred that the mold is contacted by a thermally-conductive surface of the cooler and the contacted side of the mold is opposite the cover by the holder part. After embedding, the tissue specimen may be demolded and the block containing the tissue specimen may be kept attached to the holder part, which may be used by a microtome to move the block past a knife that cuts sections. The three modules may be separate from each other, preferentially at least the first and the second modules are separate parts of the same system (i.e., the third module is not integrated with the other two modules) but all three modules may be separate parts of the same system.

Optionally, the chemical admixture is comprised of a non-aqueous solution comprising (i) at least one ketone, which may be acetone, and (ii) at least one oil, which may be mineral oil or pine oil; it may be further comprised of at least one surfactant, which may be dimethyl sulfoxide. Preferably the chemical admixture is not comprised of an aldehyde (e.g., as formalin), an alcohol, a xylene, or any combination thereof. The chemical admixture for grossing and processing is preferably the same in composition, but they may be comprised of different chemicals or in different proportions. Optionally, the matrix is comprised of at least one paraffin wax. Preferably the matrix is not comprised of an oil, a xylene, or both.

In a third embodiment, a grossing system and a grossing tool are provided.

Further aspects and advantages of the invention will be apparent to a person skilled in the art from the following detailed description and claims, and generalizations thereto.

DESCRIPTION OF SPECIFIC EMBODIMENTS OF THE INVENTION

Figure 1:
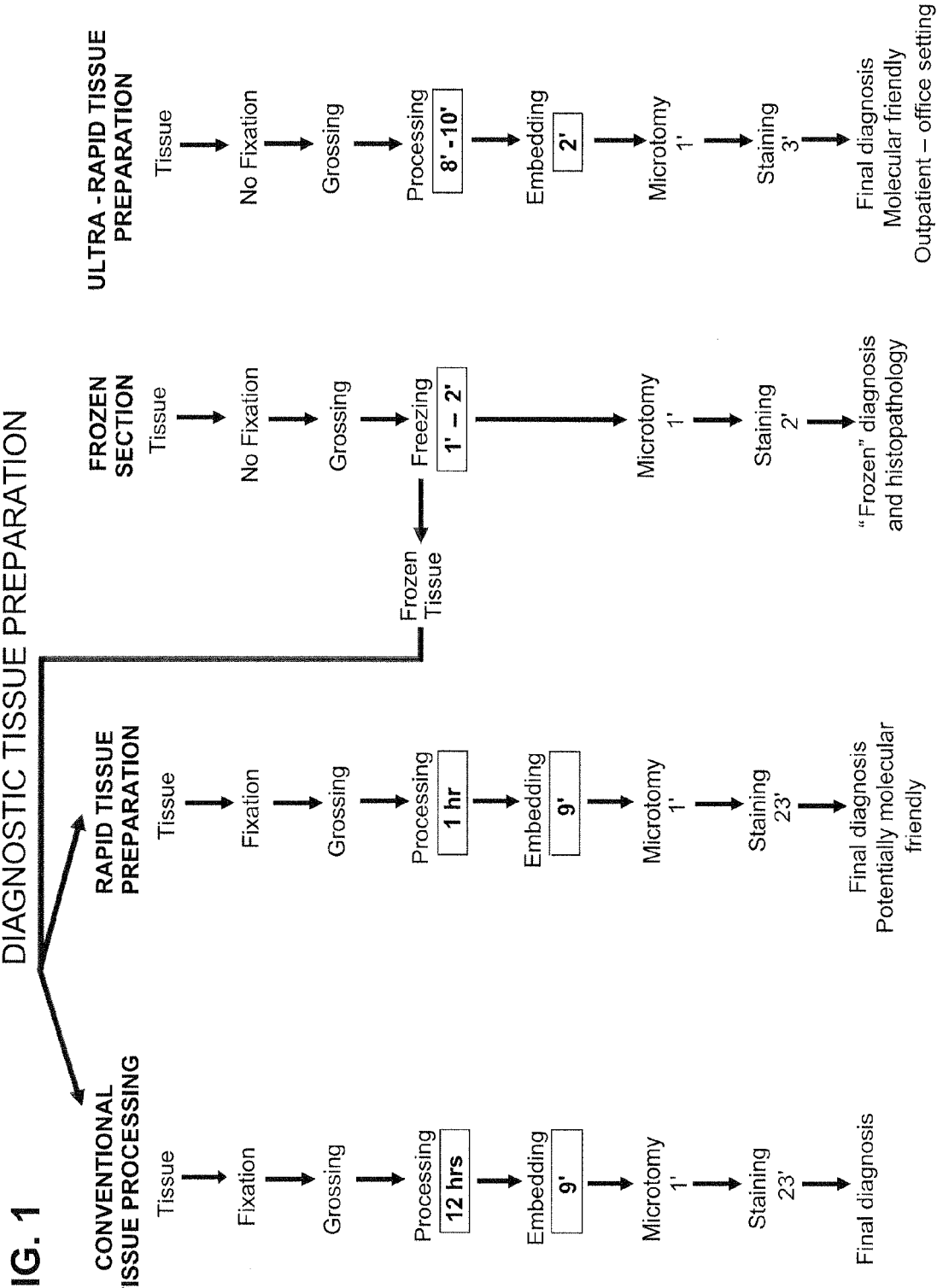
FIG. 1 shows flowcharts comparing histology (e.g., microscopic examination of a solid tissue that is sectioned and stained) of a frozen section to that of a permanent section prepared by different methods. A solid tissue is grossed. Conventional processing fixes in formaldehyde, dehydrates in a graded series of alcohol, clears in xylenes, and embeds in wax. Rapid processing hardens in ketone and alcohol using microwave energy, then impregnates under vacuum and embeds in paraffin wax using thermal energy to make permanent sections. Histology of a frozen section does not require fixing, impregnating, or embedding. Instead, a fresh sample is hardened by freezing, then sectioned without embedding in a wax block. Ultra-rapid preparation according to nonlimiting Example 1 is shown for a tissue sample that is grossed (e.g., a fresh sample is contacted with a chemical admixture to initiate hardening and ease slicing the sample into a tissue specimen thereby), the tissue specimen is processed then embedded in a block, and the block is cooled to solidify. The block is subjected to microtomy to provide tissue sections of the tissue specimen. Tissue sections are dewaxed, then stained (e.g., antibody or dye) and their histomorphology is examined.

With regard to the processing and histologic analysis of solid tissue, a tissue section must be from about 2 µm to 10 µm to be examined with magnification under a microscope, whereas the thinnest slice of fresh tissue that can be obtained using a grossing tool is more than ten times as thick. In order to produce a tissue section suitable for microscopic examination, it is thus necessary to harden the tissue so that a thinner slice can be obtained (e.g., sectioning with a microtome). A specimen about 0.6 mm in thickness is sufficient to provide about 75 tissue sections.

Microtomy of a tissue block has to produce acceptable ribbons (i.e., a series) of tissue sections that can be floated in a water bath without "exploding" and positioned on a glass slide for histological staining without "cracking" in a consistent and uniform manner over a variety of tissue types. This handling of tissue sections after cutting with a microtome is essential to provide efficient and reliable histological diagnoses based on morphology observed in stained tissue sections. Portions of the tissue section that are missing or poorly stained would defer diagnosis based on the morphology of the tissue in that section, thereby reducing confidence in diagnostic conclusions. Therefore, procedures and apparatuses that are used in a pathology laboratory require validation according to established protocols so that they can be consistently and efficiently performed; a variety of tissue types can be processed, embedded in a block, and sectioned; different diagnostic criteria for a variety of diseases can be applied to them; and histologic diagnosis (i.e., tissue morphology visualized by staining with antibody or dye) of precious samples is performed quickly and accurately. The present invention has the advantage of preparing "permanent" sections having recognized morphology for intraoperative diagnosis instead of frozen sections that have a significant incidence of discordant or deferred results.

During microtomy, poorly processed tissue specimens do not form a ribbon of serial tissue sections, the section explodes when floated in a water bath, and there are cracks (i.e., missing portions) in the tissue section. Acceptable processing results do not suffer from such defects because microtomy produces tissue sections with preserved morphology (e.g., cellular structure and tissue organization) during subsequent histologic analysis. Variable results (e.g., inconsistent morphology for sections from the same tissue specimen, or consistent for some tissue types but unsatisfactory with other tissue types) are not acceptable for histologic diagnosis.

In a first embodiment, hardening of a tissue specimen may be performed by contacting with a chemical admixture and microwave energy in a whispering gallery. A tissue specimen that was hardened may then be impregnated under vacuum by contact with a molten matrix and thermal energy. Hardening of the tissue specimen may take place with radiative heating using microwave energy at ambient pressure (e.g., 1 bar). The chemical admixture may be comprised of at least one ketone and at least one oil (i.e., alkane that is liquid under ambient condition and is derived from animal, plant, or petroleum). The chemical admixture may be further comprised of at least one surfactant. The solution hardening the tissue specimen is preferably not comprised of an alcohol, an aldehyde, a xylene, or any combination thereof. The chemical admixture and/or microwave energy may fix, dehydrate, and optionally clear the tissue specimen. This combination may decrease processing time and/or may increase quality of the tissue examined for histomorphology. Impregnation of the tissue specimen may be performed by contacting with a molten matrix and conductive heating using thermal energy (e.g., Joule heating) under less than atmospheric pressure (1 bar) to draw the chemical admixture from a tissue specimen and to impregnate the matrix into the tissue specimen. Vacuum promotes impregnation by promoting diffusion and reducing the evaporation temperature of any solvents that may be present in the tissue specimen. The matrix may comprise at least one paraffin wax and/or other waxes (i.e., alkane that is solid under ambient condition and is derived from animal, plant, or petroleum), which optionally has been degassed and dehydrated. The solution impregnating the hardened tissue specimen is preferably not comprised of mineral oil, xylene, or both. Embedding of the tissue specimen may occur by casting it and a molten matrix in a mold to produce a block. Then the block may be solidified by cooling (e.g., refrigerant compressor or Peltier effect). The embedded tissue is then sectioned with a microtome. Tissue sections are floated on water for placement on a glass microscope slide. After the tissue section(s) is placed on the slide, the matrix is removed from the slide and the remaining tissue section is adhered to the glass. The slide is then stained and coverslipped.

In a second embodiment, a tissue specimen may be hardened by contact with a chemical admixture and microwave energy in a whispering gallery, impregnated by contact with a molten matrix and thermal energy in a chamber under vacuum, and embedded in a block. Microwave energy (e.g., magnetron, klystron, traveling wave tube) or thermal energy (e.g., resistive heater or heat pump) heats the chemical admixture and the molten matrix, as well as other contents such as tissue specimens. Agitation (e.g., aeration, cycles of vacuum and increased pressure, shaking, etc.) may be used to promote exchange between a solution (e.g., chemical admixture or molten matrix) and the tissue specimen. Next, the tissue specimen is embedded in a block over a cooler unit (e.g., thermoelectric cooler or gas condenser). The tissue block may be solidified in contact with the cooler unit such that the block can be easily sectioned for histology (e.g., examination under a microscope of antibody or dye specifically bound to the tissue section).

Successful completion of tissue preparation is indicated by ease of sectioning of tissue embedded in a block during microtomy and preservation of morphology during histologic examination of tissue sections. Although semi-automated operation of the method and system is preferred with manual transfer into the microwave unit and automated transfer between microwave unit and vacuum unit (optional are automated transfer out of the vacuum unit and an unloading station), the chemical admixture (or molten matrix) may be transferred between a whispering gallery and an optional first reservoir (or a chamber and an optional second reservoir) that are in fluid communication with each other (e.g., tubing or piping, valves, and pumps with control circuitry to determine the timing, speed, and direction of flow for a solution).

A tissue specimen may be hardened with an admixture of chemicals, which may be a non-aqueous solution comprising at least one ketone (e.g., acetone, methyl ethyl ketone) and at least one oil (e.g., mineral oil, pine oil). For the non-aqueous solution of ketone(s) and oil(s), the volume ratio of the two agents may be between about 12:1 to about 6:1 (although such extremes may change the processing time or results may be less reliable); less than about 12:1, less than about 11:1, or less than about 10:1; more than about 6:1, more than about 7:1, or more than about 8:1; about 9:1, or any intermediate range thereof (e.g., between about 10:1 to about 8:1). The chemical admixture may be further comprised of a surfactant that may accelerate hardening: e.g., dimethyl sulfoxide (DMSO), polyoxyethylene sorbitan esters (e.g., TWEEN 80), sodium dimethyl sulfosuccinate, mild household detergents, or the like. The chemical admixture may also be buffered with the appropriate use of acid and base, but acetic acid does not need to be included in the non-aqueous solution.

The tissue specimen may be incubated in the chemical admixture for a time period between about 3 minutes and about 6 minutes; greater than about 3 minutes, greater than about 4 minutes, or greater than about 5 minutes; less than about 4 minutes, less than about 5 minutes, or less than about 6 minutes; or any intermediate range thereof (e.g., from about 4 minutes to about 5 minutes). The temperature may be between about 40° C. and about 60° C.; greater than about 45° C., greater than about 50° C., greater than about 55° C., or greater than about 60° C.; less than about 60° C., less than about 65° C., less than about 70° C., or less than about 75° C.; or any intermediate range thereof (e.g., between about 45° C. and 55° C.).

A tissue specimen may be impregnated with a molten matrix, which may be a wax solution comprising at least one paraffin wax. Preferred matrices are commercial wax formulae, mixtures of waxes of different melting points (waxes are solid at room temperature and have melting points which are dependent on their chain lengths, while mineral oil is liquid at room temperature), and the like. They may be further comprised of one or more additives to change the crystallization properties of the matrix. The tissue specimen may be incubated in the molten matrix for a time period between about 3 minutes and about 6 minutes; greater than about 3 minutes, greater than about 4 minutes, or greater than about 5 minutes; less than about 4 minutes, less than about 5 minutes, or less than about 6 minutes; or any intermediate range thereof (e.g., from about 4 minutes to about 5 minutes). The wax solution may be a solid at room temperature (e.g., below about 25° C. or below about 30° C.) and molten above about 55° C. or above about 60° C. The temperature may be between about 50° C. and about 70° C.; greater than about 50° C., greater than about 55° C., greater than about 60° C., or greater than about 65° C.; less than about 65° C., less than about 70° C., less than about 75° C., or less than about 80° C.; or any intermediate range thereof (e.g., between about 55° C. and 65° C.). It is preferred that the incubation be conducted under reduced pressure (e.g., above about 0.5 bar, above about 0.6 bar, or above about 0.7 bar; below about 0.7 bar, below about 0.8 bar, below about 0.9 bar, or below about 1 bar; or any intermediate range thereof).

Prior to sectioning, the impregnated tissue specimen may be embedded in the same matrix to form a tissue block. For example, the impregnated tissue specimen may be placed in a metal mold, more molten matrix may be added to fill the mold and to form the tissue block, and the tissue block may be held on a platform (e.g., previously used cassette or other holder having identification information) that attaches to a microtome for sectioning. Embedding may be accelerated by cooling the mold on dry ice, in a bath containing an organic solvent and dry ice or a bath containing a mixture of organic solvent and liquid nitrogen, or on a surface of a cooler unit with a compressed refrigerant or Peltier cooling source. In one embodiment, the block is solidified by cooling at a temperature of below about −50° C., below about −25° C., below about 0° C., below about +5° C., above about −200° C., above about −100° C., above about −50° C., above about −25° C., or at a temperature in any range therebetween. After sectioning, the matrix (now solid) may be removed by melting at a temperature above about 100° C.

A whispering gallery or reaction chamber may be comprised of any combination of the following: a lid adapted to isolate it from its surroundings and to provide access to its contents (e.g., made from a material opaque to microwave radiation and/or visible light); a gasket (e.g., made from rubber or silicone) between the lid and the whispering gallery or reaction chamber to retain chemical fumes in the former (as well as optional heated reservoir) and/or to maintain a reduce pressure in the latter; thermal insulation to retain heat in the whispering gallery or reaction chamber; at least one temperature and/or pressure probe to monitor conditions therein; a seal to isolate electronic components from chemicals and condensation in the whispering gallery or reaction chamber; and control circuitry which receives input from at least one probe and/or timer. Similarly, a heated reservoir may be comprised of any combination of thermal insulation, at least one temperature and/or pressure probe, a seal, and control circuitry which receives input from at least one probe and/or timer.

In a preferred embodiment, the chemical admixture is pre-mixed and stored in a bottle prior to use. The bottle is opened and at least some of its contents drawn into a (first) reservoir to be preheated, transferred into the whispering gallery of the first module before entry of the tissue specimen, and transferred back to the (first) heated reservoir to drain the whispering gallery before the tissue specimen is moved (either manually or automatically) to the second module. Solid matrix may be melted directly in the chamber of the second module. Alternately, it may be melted in a (second) heated reservoir, and then drawn into that chamber. The chemical admixture may be transferred between (first) heated reservoir and whispering gallery of the first module during tissue processing. In contrast, the molten matrix may be maintained in the reaction chamber of the second module during tissue processing. At the end of the day, the chemical admixture may be drawn back into the bottle, the molten matrix may be drawn back into the second reservoir, then they may be safely disposed or stored for reuse.

Alternately, a single reaction chamber may be used within a module which combines both microwave and vacuum functions in a single unit. In succession, the chemical admixture and the molten matrix may be transferred from separate first and second reservoirs, respectively, to the common reaction chamber and back again.

Such system may be manually operated or automated (i.e., transfer of tissue specimen between modules with a mechanical conveyance). The system may be further comprised of a loading and/or unloading station. Tissue specimens may be loaded into the system and processed either in batches or as separate specimens. Tissue specimens may enter the system at the loading station and exit the system from the unloading station where they are optionally collected. Control circuitry (e.g., computer and its program) may be used to move tissue specimen(s) through the system, to prevent access to the reaction modules during operation, to modify one or more reaction parameters (e.g., time, temperature, pressure, or amounts of solution in the method), or any combination thereof.

A tissue specimen is a solid block can be mounted on a microtome to produce tissue sections of between about 1 micron and about 50 microns, or between about 2 microns and about 10 microns. Tissue sections may be further processed for histochemical staining, antibody binding, in situ nucleic acid hybridization or amplification, or a combination thereof. For example, a plurality of tissue sections adhered to glass may be heated to a temperature above about 100° C. to melt the solidified matrix, the molten matrix is removed, the remaining tissue sections on glass are stained with an antibody or dye, and visualized with magnification under a microscope. But other techniques for detecting cellular properties may be used to examine the processed tissue specimen (e.g., fingerprinting of fragments, fractionation and blotting, sequencing). Tissue blocks may be stored for archival purposes or retrospective studies.

Cell phenotypes (e.g., reactivity with cell-specific antibody, chemical staining) may be analyzed by removing the solid matrix (e.g., dewaxing) and dissecting tissues (e.g., proteolytic digestion and mechanical disaggregation). Individual cells may be dispersed in a spray and analyzed in a flow cytometer. Alternatively, dewaxed tissue sections may be mounted on a microscope stage, dissected with a laser and/or micromanipulator into substantially homogeneous cell populations, and the different cell types analyzed by physical, chemical, or genetic techniques.

The present invention is compatible with preparation of nucleic acids, DNA or RNA, from processed tissues. Thus, genetic study is possible for tissue specimens collected routinely in the clinical pathology laboratory. The combined power of these technologies will be great. Histological observations may be correlated with genetics by analyzing a tissue section by staining (e.g., specific antibody or dye), and preparing nucleic acids from an adjacent tissue section for genetic analysis. For example, diseased and normal regions of the same tissue section may be compared to detect genetic differences (e.g., mutations, levels of transcription), disease progression may be characterized by comparing genetics differences in samples taken at several time points, and tumor evolution may be assessed by following the accumulation of genetic differences from primary cancer to metastasis. Substantially homogeneous or merely enriched cells may be obtained by sorting cells from a tissue section with a flow cytometer or microdissection.

Mutations may be germline and used to trace genetic predisposition of disease, or mutations may be somatic and used to determine genetic alterations in disease pathogenesis. The disease may be a metabolic or neurologic disorder, malignancy, developmental defect, or caused by an infectious agent. The present invention preserves material for genetic analysis by a simple procedure and room temperature storage. It may be analyzed by in situ hybridization or nucleic acids may be extracted from tissue.

Hematoxylin-eosin staining is commonly used for histological study and may be considered a standard for comparison by other anatomic pathologists. In addition, other stains may be compatible including trichrome, reticulin, mucicarmine, and elastic stains as described in general references such as Thompson (*Selected Histochemical and Histopathological Methods*, C. C. Thomas, Springfield, Ill., 1966), Sheehan and Hrapchak (*Theory and Practice of Histotechnology*, C. V. Mosby, St. Louis, Mo., 1973), and Bancroft and Stevens (*Theory and Practice of Histological Techniques*, Churchill Livingstone, New York, N.Y., 1982). Such staining procedures would take between 30 minutes and several hours to complete, although rapid staining procedures are available from Fisher Scientific that require only five minutes.

Solid tissue may be obtained from surgical biopsy or resection. During cancer surgery, the ability to provide a pathological diagnosis from a stained tissue section will provide the surgeon with information that may be used prior to the patient's departure from the operating room (i.e., intraoperative diagnosis). For example, an indication from the anatomic pathologist that the cancer is confined to the resected tissue may allow the surgeon to be conservative in treatment and to preserve neighboring healthy tissue. Alternatively, a finding by the anatomic pathologist that cancer is not confined to a resected organ would permit more aggressive surgical treatment while a patient was still in the operating room. In contrast to conventional histologic examination of a frozen section, ultra-rapid diagnostic preparation of a fresh specimen may provide tissue sections having better histomorphology and reduce the need for later confirmation using a paraffin section from the same tissue that the frozen section was obtained.

Exemplary tissues that may be processed include: appendix, bladder, bone, bowel, brain, breast, carcinoma, cervix (squamous epithelium), gall bladder, heart, kidney, liver, lung, ovary, parotid gland, placenta, prostate, skin, spleen, testicle, thyroid gland, tonsil, and uterus (myometrium and endometrium). Lymphoreticular and fatty tissues may also be processed. Mineralized tissue would require decalcification prior to processing by the present method. Subsequent analysis would include detecting DNA mutations and RNA expression, genomic analysis, histochemistry, immunochemistry, and proteomic analysis.

Tissue sections may be further processed for antigen recovery and/or preservation. Non-specific binding sites are blocked, antigen is bound by specific antibody (i.e., the primary antibody), and non-bound specific antibody is removed. The antigen may be protein, carbohydrate, or ganglioside; its antigenic determinant may be linear or nonlinear amino acids, sugars, other modifications, or a combination thereof. If the antibody is labeled with a probe or signal generating moiety, a primary antibody may be detected directly but it is preferred to attach the probe to an amplifier (e.g., secondary antibody) that specifically binds the primary antibody. Secondary antibody may be raised against the heavy or light chain constant region of the primary antibody. This amplifies the signal generated by an antigen-antibody conjugate because each primary antibody will bind a plurality of secondary antibodies. Amplification may occur through other specific interactions such as biotin-streptavidin. Antibody binding may be performed in a small volume to reduce usage of expensive reagents and maintain a high binding rate; evaporation of this small volume may be reduced by incubation in a humidity chamber. The signal generating moiety is preferably an enzyme that is not otherwise present in the tissue. For example, alkaline phosphatase and horseradish peroxidase may be attached to the secondary antibody or conjugated to streptavidin. Substrates are available for these enzymes that generate chromogenic, fluorescent, or luminescent product that can be detected visually.

The staining pattern for antigen may be used to localize expression of the antigen in the context of cellular structures revealed by counterstaining. Antigen expression can identify cell or tissue type, developmental stage, tumor prognostic markers, degenerative metabolic processes, or infection by a pathogen.

Antigen-antibody binding may also be visualized with fluorescent, radioactive, or colloidal metal probes by epifluorescence, autoradiography, or electron microscopy. Similar probes may be used to detect nucleic acid in the tissue section by in situ hybridization to identify genetic mutations or transcripts; alternatively, the nucleic acid (DNA or RNA) may be extracted from tissue sections and analyzed directly by blotting, or amplified prior to further genetic analysis.

Tissue preparation may be integrated with other modules: (i) grossing module that produces a tissue specimen from fresh tissue; (ii) embedding and sectioning modules that produce a block of matrix-embedded tissue specimen and tissue sections thereof; (iii) microtomy, staining, and coverslipping modules that provide slides containing tissue sections; (iv) developing module that visualizes histochemical and/or immunochemical signals on tissue sections; (v) microdissection module that separates cells of the tissue section into substantially homogeneous populations; (vi) imaging module that scans tissue sections on a slide, digitizes signals visualized through a microscope, and then manipulates, stores, and transmits those images; and any combination thereof. Tissue, especially after sorting and/or separating into substantially homogeneous populations, may be analyzed by their DNA or RNA sequences, genetic mutations, changes in the level or pattern of gene expression, changes in the level or pattern of protein expression, and combinations thereof. System integration and data management are facilitated by identifying each tissue specimen or its holder by alphanumeric characters, bar code, near field or radiofrequency identification, or other labeling. Identical or different labels may be used to identify a particular tissue specimen as its proceeds through a series of mechanical systems. The labels and other information about the tissue specimen (e.g., patient name, date, location in the facility, disease or other pathological condition, tissue type, diagnosis, phenotype, genotype, genomic or proteomic characterization) may be entered into a database management system to store, manipulate, and retrieve the data. Mining such information in the database may prove or disprove correlations in accordance with statistical criteria, and suggest further investigations.

A first step in the method, which may be carried out in the surgical theater, pathology laboratory, or elsewhere, is to provide a sample of tissue suitable for ultra-rapid diagnostic preparation. Subsequent steps take place outside the patient's body (ex vivo), and preferably not even in the presence of the patient. Typically, grossing provides a slice of the tissue of interest. Alternatively, a fine slice or needle may be obtained during biopsy. For solid tissue, a sample prepared by grossing provides a tissue specimen from about 0.4 mm to about 0.8 mm, more preferably from about 0.5 mm to about 0.7 mm, and most preferably about 0.6 mm as measured in the smallest dimension (i.e., thickness). Preferably, hardening may be initiated, but not completed, by grossing solid tissue in contact with a chemical admixture. The step of grossing may be performed in a time period between about 5 seconds and about 5 minutes; greater than about 1 minute, greater than about 2 minutes, or greater than about 3 minutes; less than about 3 minutes, less than about 4 minutes, or less than about 5 minutes; or any intermediate range thereof (e.g., from about 10 seconds to about 3 minutes). For example, a resected piece of a patient's organ may be placed in a tissue-receiving depression of a grossing board, which contains a chemical admixture, with the tissue supported by the depression's bottom surface. A tissue specimen to be processed may be sliced to a substantially uniform thickness by a blade guided along metal rails over the board's top surface, which may be substantially even with the depression's top surface, while optionally in contact with the chemical admixture to initiate hardening and thereby facilitate taking a thin slice. After grossing, the tissue specimen is placed in a cassette or other holder in which it is contained during subsequent processing until the tissue specimen embedded in a block ready for sectioning. The block is solidified by cooling and thereby facilitates sectioning with a microtome. Alternatively, a tissue specimen of suitable thickness may be provided by coring or snipping tissue with a trochar (e.g., for biopsy) instead of grossing, then placed in a cassette or other holder. Although manual processing is preferred, the cassettes may be placed in a carrier or basket for ease of handling. The cassette or holder is next placed in a chemical admixture, preferably manually.

To reduce processing time, it is recommended to reduce the thickness of a tissue sample on a grossing board such as described in WO 01/96830 or WO 2010/027430 to provide a tissue specimen, wherein a chemical admixture such as used for tissue processing fills a depression in the grossing board where the tissue sample is placed for slicing to a substantially uniform thickness (see Example 3). For simplicity, it is preferred that the same chemical admixture be used for grossing and hardening.

A tissue specimen, cassette, or holder is exposed to the chemical admixture that hardens the tissue specimen while simultaneously being heated by microwave energy and optionally agitated. Only a single microwave unit is needed because one chemical admixture can be used. The hardening solution may remain in a whispering gallery through several cycles of processing, or may be transferred between the whispering gallery and a reservoir at intervals (e.g., removed to reservoir after every hardening cycle, when all tissue specimens have been processed, or at the end of operations during the day). A carrier of specimens or cassettes containing a tissue specimen may be preferably transferred between reaction chambers manually, or by an armature or track conveyance.

To provide for agitation which accelerates processing, a chemical admixture or molten matrix may be aerated. To provide more uniform agitation by air, a diffusion plate at the bottom of a whispering gallery or reaction chamber and across a substantial portion thereof may be used for uniform aeration of the entire volume of solution. Agitation may also be provided by pressure and vacuum (PN) cycles (e.g., periods of a few seconds each spent under pressure, reduced to a partial vacuum, and under pressure again) or pumping solution into and out of the whispering gallery or reaction chamber (e.g., circulating the solution throughout) or using PN cycles.

In a preferred embodiment, the system for preparing a tissue specimen can be limited to three or four discrete modules: an optional grossing unit, a microwave unit, a vacuum unit, and an optional cooler unit. Grossing of a fresh sample of solid tissue provides one or more tissue specimens by contacting with a chemical admixture that initiates hardening and slicing to a substantially uniform thickness. A tissue specimen is contacted with the same or a different chemical admixture and microwave energy to complete hardening in a microwave unit. The hardened tissue specimen is then contacted with a molten matrix and thermal heat to initiate impregnating in a vacuum unit. Processing takes place in a reaction chamber (also known as a retort or vessel), which has an interior shaped as whispering gallery (e.g., microwave unit) or cylinder (e.g., vacuum unit). Only one microwave unit and one vacuum unit are required; they may be integrated in the same unit. Agitation therein may be provided with a mechanical device that causes aeration in, shaking or vibration of, or transfer of ultrasound energy into the solution. Alternatively, a pump may be used for agitation using PN cycles or circulating the solution. Embedding of the hardened and impregnated tissue specimen in a block may be cast (with additional molten matrix) in a mold. A tissue block may be solidified over an optional cooler unit in contact with a surface that conducts thermal energy from the tissue block.

A microwave unit may be comprised of (i) a source of microwave energy (e.g., circuit comprised of cavity resonator and an optional waveguide that transmits the microwave energy from the source to a whispering gallery, its dimensions and shape adapted for this purpose) and (ii) a whispering gallery that receives the transmitted microwave energy and is adapted to process a tissue specimen by hardening. The whispering gallery may contain a plurality of different specimens. Preferably, the interior geometry of the whispering gallery is configured to achieve uniform distribution of microwave energy and heating of its contents. Uniformity is achieved primarily by consideration of two factors.

First, the circumference of the whispering gallery is made to be an integral number of half wavelengths of the radiation therein. With proper arrangement of the waveguide entrance into the whispering gallery, a mode will be excited that will propagate around the exterior wall. This type of mode is characterized by the microwave field being predominantly near the exterior wall. A similar phenomenon occurs in acoustics where sound waves travel very efficiently next to solid walls. These types of modes are referred to as whispering gallery modes.

A second consideration is the radial distance between the boundary of solution in the whispering gallery and its wall. The optimum spacing is determined empirically by changing that spacing. If spacing is too narrow, the microwave energy is absorbed primarily near the entrance to the reaction chamber. If spacing is too wide, the whispering gallery becomes a resonant cavity and is sensitive to the amount of chemical admixture and solids (e.g., specimen, cassettes, or carrier) therein. With the proper spacing, efficient heating of the solution and solids is achieved over an extensive range of heights of the contents as measured by a level sensor outside the whispering gallery (i.e., volumes therein). As little as 10% of the full height (i.e., total volume) still provides efficient heating of the contents.

Similarly, the source and the waveguide are configured to achieve minimal energy loss during transmission of the microwave energy. The microwave unit is configured with a waveguide to have no more than about 2% energy loss from the source to the whispering gallery. A higher energy loss would require the use of expensive shielding and other protection devices for the source of the microwave energy.

Heating may be controlled by cycling power on-off in cycles of about 10 to 25 seconds because a minimum time is required by the heating characteristics of the cathode of the microwave source. But this may burn the tissue, so heating may be controlled through a variable current source to allow continuous variation in the power delivered by the microwave source to the reaction chamber. Such burning or over cooking is typified by homogeneous staining of tissue structures without distinguishing cellular features. The latter is preferred to reduce peak power output. The microwave unit may be further comprised of any combination of a container adapted to fit in the reaction chamber and to receive at least one tissue specimen (e.g., a basket); at least one temperature and/or pressure probe to monitor conditions in the reaction chamber; one or more energy probes to monitor microwave energy being sent by the source, transmitted through the waveguide, and/or received by the reaction chamber; a closure adapted to fit the reaction chamber and to isolate the reaction chamber from the operator's surroundings; thermal insulation to retain heat in the reaction chamber; shielding to isolate electronic components from chemicals in the reaction chamber; and control circuitry to receive input from at least one probe or timer and thereby regulate at least one of the microwave energy from the source, transmitted through the waveguide, and/or received in the reaction chamber. The container is preferably transparent to microwave radiation and therefore energy is not consumed in its heating.

The material used for the vacuum seal may be chosen for its ability to hermetically isolate a reaction chamber or a reservoir from the environment, malleability to ensure a tight fit that conforms to the lid, and chemical resistance to solutions of the method. Modifying a reaction chamber or reservoir with (i) a lid and a gasket/seal to reduce evaporation and (ii) thermal insulation can reduce the power required to operate the microwave unit or the vacuum unit by two or three-fold.

The modules may occupy the same space and/or the tissue specimen may remain stationary. Microwave or thermal energy may be regulated and transmitted into the same space, or onto the stationary tissue specimen at different times in the method. Chemical solutions and/or vapors may be moved into or out of the same space, or brought into or out of contact with the stationary tissue specimen. Preferred is minimizing space requirements for the system by using two reaction chambers, and transporting the different chemical compositions into a reaction chamber by tubing or piping from separate storage and/or waste chambers. A controller can receive input from the reaction chamber and/or from timing that part of the processing cycle, and thereby regulate the transport of the different chemical compositions.

Either transferring different solutions into and out of a reaction chamber or transferring the basket between reaction chambers containing different solutions may effect changes in processing steps. Holding the basket above the interior of a reaction chamber for a few seconds allows excess solution to drain back through one or more openings in the bottom and/or sides before the basket is transferred. Thus, the sequence in which the basket is transferred between reaction chambers, each containing a particular composition of tissue processing chemicals, and the time the basket is incubated in each reaction chamber will dictate the series of chemical reactions necessary to accomplish the method according to the invention.

The lid can be removed; the gasket can be attached to the lid and moved with it. This procedure of removing the lid and gasket is performed for both the current unit that contains the tissue specimen(s) and the next unit into which tissue specimen(s) will be subsequently transferred. The basket is then removed, remaining chemical admixture may drain from the basket and cassettes that may be contained therein back into the reaction chamber for a few seconds, and the basket may be transferred to the next reaction chamber containing molten matrix. Flushing of the tubing/piping and cleaning of the reaction chamber are not required because the amount of solution left behind is minimal. Finally, the lids and gaskets are replaced. The total time for such a transfer is about one minute.

In accordance with the invention, variations on the above embodiments are envisioned. Various configurations of the tissue processing system are possible, and optional modules may be connected to form a portion of the system. The specific configuration chosen may be dictated by the average number of tissue specimens that will be processed on a daily basis by the clinical laboratory, and/or the speed with which histology or pathology reports must be prepared.

The system may be manually operated or automated. Manual operation is particularly suited for facilities quickly processing a single tissue specimen or a small number of tissue specimens. For an automated system, a tissue specimen may be transported by a mechanical conveyance (e.g., robot arm, track formed by belt and roller) and/or chemical compositions may be transferred by corrosion-resistant plumbing. Thus, processing may be automated by transferring tissue specimens between stationary modules in a particular sequence, filling and emptying modules of different chemicals such that stationary tissue specimens are incubated in a particular sequence, or any combination thereof. Programs which control parameters of tissue processing (e.g., startup and shutdown of system, loading and unloading a number of tissue specimens, conditions such as reaction time, progress of tissue specimens through the system) may be monitored on a screen; parameters of tissue processing (e.g., one or more tissue specimen in reaction chamber for about 2, 3, 4, 5, 6 or 7 minutes, from about two to about seven minutes, or any intermediate range therebetween) may be preset or selected by the operator through a keypad.

The armature conveyance may, for example, grab a carrier containing one or more tissue specimens with a pincer-like mechanism or catch the carrier with a hook-like device. The arm may be articulated to perform human-like motion; or may be mounted in a fixed coordinate rack with linear or two dimensional movement, and optionally another dimension of movement provided by varying the height of the arm over the system. The track conveyance may be made from resilient or tacky material to fix a carrier containing one or more tissue specimens on the track by friction, or there may be a regular series of bumps or walls to trap the carrier therebetween. The track may be formed as a continuous belt or may be a series of belts that convey the carrier, with the belt put into motion with a roller or sprocket mechanism. The carrier may be a basket, containing a plurality of cassettes each having a single tissue specimen, that is adapted for conveyance by having a stem (with or without a knob) to be grabbed or a loop to be caught by the arm, or fitting within a groove or indentation of the track. Alternatively, the carrier may contain a single or a few tissue specimens (e.g., one cassette), the carrier being adapted for transport by the armature or track conveyance.

Electric motors and controllers may be used to transport a tissue specimen by the operator's real-time command or selection of a program stored in computer memory. A simple mechanism of controlling the time spent by the tissue specimen in each module would be to move the tissue specimen or carrier thereof at a constant speed and to adjust the length of the path through each module to accommodate the intended incubation time.

The flexible tubing or rigid piping, as well as other plumbing components, should be made of chemical-resistant materials to prevent corrosion (e.g., glass, stainless steel, polyethylene, polytetrafluoroethylene, polyvinylchloride). Controllers and pumps/valves may be used to transport chemical compositions (e.g., chemical admixture and/or molten matrix) from storage chamber to reaction chamber, from reaction chamber to storage chamber if the composition can be reused, and from reaction chamber to waste chamber if the composition is to be flushed from the system; to fill the storage chamber; and to flush the waste chamber by the operator's real-time command or selection of a program stored in computer memory. Vapor seals and/or cooling may be necessary to isolate corrosive vapors of the chemical admixture from mechanical and electrical components of the system. A heated reservoir and heated plumbing components may be necessary to maintain the composition at reaction temperature or to ensure that the molten matrix is kept in a transportable fluid state.

All of the patents, patent applications, and other publications cited herein are incorporated by reference in their entirety.

The following examples are meant to be illustrative of the present invention, but the practice of the invention is not limited or restricted in any way by them.

EXAMPLES

Example 1

Fresh (i.e., neither frozen nor prefixed) tissue was grossed to a substantially uniform thickness of about 0.6 mm (e.g., from about 0.4 mm to about 0.8 mm) to provide one or more tissue specimens for processing. It is preferred that hardening is initiated while solid tissue is being sliced by contacting fresh tissue with a chemical admixture, which may be the same or different from the chemical admixture used for processing (see below), during grossing. Fresh samples from a variety of different residual tissues and diseases affecting skin, lung, spleen, liver, uterus, placenta, bowel, ovary, carcinomas (e.g., breast, kidney, and testis), sarcomas, and leiomyomas were prepared as permanent sections according to a novel process.

Tissue specimens were processed in a chemical admixture comprised of about 90% (v/v) acetone, about 10% (v/v) mineral oil, and about 0.1% (v/v) dimethyl sulfoxide (DMSO). The two major components were mixed in a volume of 3.8 L, and 5 ml of DMSO was added thereto. Tissue specimens were incubated for about 4-5 minutes in this chemical admixture at about 50° C.; solution exchange was promoted by agitating the chemical admixture (e.g., aeration). Both the tissue specimen and the chemical admixture were heated by microwave energy.

Following hardening of the tissue specimen, it was impregnated for about 4-5 minutes in molten paraffin at a temperature of about 62° C. under reduced pressure (about 640 mm of Hg). Impregnation was promoted by agitating the molten paraffin with P/V cycles. After a total processing time of about 8-10 minutes, tissue specimen was embedded in the molten paraffin. The hardened and initially impregnated tissue specimen and molten paraffin were cast in a metal mold, then they were contacted with dry ice (about −78° C.) for about 1-3 minutes. The solidified block containing tissue specimen was sectioned with a microtome, tissue sections were floated on liquid, gathered as serial sections on a glass slide, and paraffin wax was removed by melting in an oven (about 104° C.). The dewaxed specimen was ready for subsequent histological analysis (e.g., stained and coverslipped), chemical analysis (e.g., isolating protein, DNA, or RNA from tissue sections or a portion thereof by extraction and at least partial purification), or stably stored at room temperature.

Example 2

Tissue processing may be performed using an embodiment of the invention (shown in FIG. 2) in the following manner. In the microwave unit, chemical admixture and microwave energy contact a tissue specimen in a chamber having an interior shaped as a whispering gallery to harden the tissue specimen. Radiation source M provides microwave energy in a hardening module. Agitation in the microwave unit may be provided by aeration (pump BP). Chemical admixture may be transferred between its reservoir and its chamber using a line regulated by valves, level sensors, and a pump LP. In the vacuum unit, hardened tissue specimen is then contacted with a molten matrix and thermal energy under vacuum (pump AP) in a chamber for impregnation. Joule heating source H provides thermal energy in an impregnating module. Agitation in the vacuum unit may be provided by PN cycling using the same pump AP, which may also transfer molten matrix between its chamber and its reservoir through a line regulated by valves and level sensor. Any transfer of a tissue specimen into and/or out of a unit may be manual or automated; transfer between the microwave unit and the vacuum unit is preferably automated. In the cooler unit, the hardened and impregnated specimen is embedded in a mold, which is solidified in contact with a thermally-conductive surface until a block of solid matrix is formed. Heat is drawn from the mold by a Peltier cooling source C in an embedding module.

A chemical admixture is manually or automatically transferred to a hardening module and paraffin pellets are added to an impregnating module. The chemical admixture is pre-warmed and the paraffin is melted prior to processing of a tissue specimen. Vacuum is drawn and pressure is raised to transfer solutions, if needed. Solution within the whispering gallery 2 or the reaction chamber 3 is agitated by bubbling (pump BP) or PN cycling (pump AP), respectively. The air pressure may optionally be used to transfer solutions from a reservoir to a whispering gallery or reaction chamber of a microwave unit. A fluid connection (e.g., flexible tubing) and a port where the connection joins different components of the system may be used to transfer solution between a first reservoir and whispering gallery using a pump LP and solenoid valves. Only impregnation in a vacuum unit may require reduction in the pressure with an air pump because processing in the microwave unit (e.g., hardening and initial impregnation) may be performed at atmospheric pressure.

Solutions and reaction chambers are warmed to appropriate operating temperatures. For example, the chemical admixture may be preheated by an electric heater in the first reservoir 1 of the microwave unit prior to transfer into its whispering gallery 2, and solid matrix is melted with thermal energy (e.g., Joule heating source) in the second reservoir 4 of the vacuum unit prior to transfer of molten matrix to its reaction chamber 3. Such transfers are typically done at the start of (daily) operation from the reservoirs and then returned to the reservoirs at the end of (daily) operation. The temperature of the chemical admixture is maintained at about 50° C. in the microwave unit by a microwave heating source M; the temperature of the molten matrix is maintained at about 62° C. in the vacuum unit by a radiative heating source R. Tubing and valves between (i) first reservoir 1 and whispering gallery 2 or (ii) second reservoir 4 and chamber 3 provide two-way fluid communication. Reservoir 1 and reservoir 4 for chemical admixture and molten matrix, respectively, are separate. The presence or absence of solution and/or basket in a microwave or vacuum unit may be determined using one or more level sensor(s) to detect volume or displacement of solution.

A perforated basket containing tissue specimens in cassettes is loaded. A loading station is optional so the basket may be placed in an empty reaction chamber of the loading station (if present) then automatically transferred by a conveyance to the whispering gallery 2. But manual transfer of the basket to the whispering gallery 2 is preferred (i.e., no loading station). The whispering gallery 2 containing a chemical admixture is heated by microwave energy. The conveyance is preferably a robot arm with a hook which reversibly attaches to the basket; a pan with a replaceable absorbent liner is attached to the robot arm and swivels under the basket to catch dripping chemical admixture or molten matrix (not shown). A lid is attached to the whispering gallery or the reaction chamber by a hinge; each lid forms a seal with the whispering gallery or reaction chamber using a rubber gasket, and is opened/closed by a chain driven with an electric motor (not shown), Automated transfer of the basket between the whispering gallery 2 and the reaction chamber 3 is preferred. Finally, when tissue processing is complete, the loaded basket is transferred from the reaction chamber 3. An unloading station is optional so the basket may be placed in an empty reaction chamber of the unloading station (if present). The time required to transfer a basket between stations is less than about 10 seconds. Tissue cassettes can be removed from the basket after processing for subsequent microtomy and staining (see FIG. 1).

The method described in Example 1 may be used in this system. A pre-heated chemical admixture is transferred from first reservoir 1 to whispering gallery 2 prior to addition of a basket containing tissue specimens into the microwave unit. Similarly, molten matrix is transferred from second reservoir 4 to chamber 3 prior to addition of a basket containing tissue specimens into the vacuum unit. The basket is transferred into the whispering gallery 2 such that one or more tissue specimens contact the chemical admixture, the lid of the whispering gallery is closed, and the one or more tissue specimens continue hardening under the influence of microwave radiation. When incubation is complete (i.e., tissue specimens are suitably hardened), the lid is opened and the basket is transferred to the reaction chamber 3 containing molten matrix, and the one or more tissue specimens are incubated therein until processing is completed.

The reaction chamber 3 containing molten matrix is conductively heated with a Joule heating source. Alternatively, an electrical heater maintains the temperature of water circulating in tubing in contact with the matrix to keep it molten. For example, tubing can be coiled inside reaction chamber 3; this heating coil would then transfer heat to the contents. Preferably the heating coil is eliminated by wrapping the outside wall of the reaction chamber with electrical wire that conducts heat through the walls into the contents of the reaction chamber. Agitation in the vacuum unit can be performed by PN cycles of nominal pressure 0.35 Kg/cm$^2$ and 500 mm Hg vacuum.

Each hardened and initially impregnated tissue specimen is cast in a mold 5 containing molten matrix. The filled mold is then cooled by contact with a cooler unit having a surface 6 conductively heated with a Peltier cooling source. The cooler unit may or may not be integrated in the same system as the microwave and vacuum units. Similarly, a grossing unit (not shown) may or may not be integrated in the same system as the microwave and vacuum units.

Other conditions (e.g., times and temperatures of incubations) are described herein. The system may be enclosed in a cabinet to contain any fumes which may be present and to vent them (fume control). A tabletop system may use an automated conveyance to transfer tissue specimens or they may be manually transferred. Alternatively, a door with a glass window at torso height allows the operator to access the system when there is no movement of the basket, to load a basket in or to unload a basket from the system, and to observe movement of the basket. For safety, it is preferred that the door locks when the arm or lid on a whispering gallery or reaction chamber is moving. Another door at knee height allows the operator (i) to attach a bottle of the chemical admixture to a port leading to the first reservoir 1 which is connected to the microwave unit and (ii) to melt paraffin in the second reservoir 4 which is connected to the vacuum unit.

Figure 3:
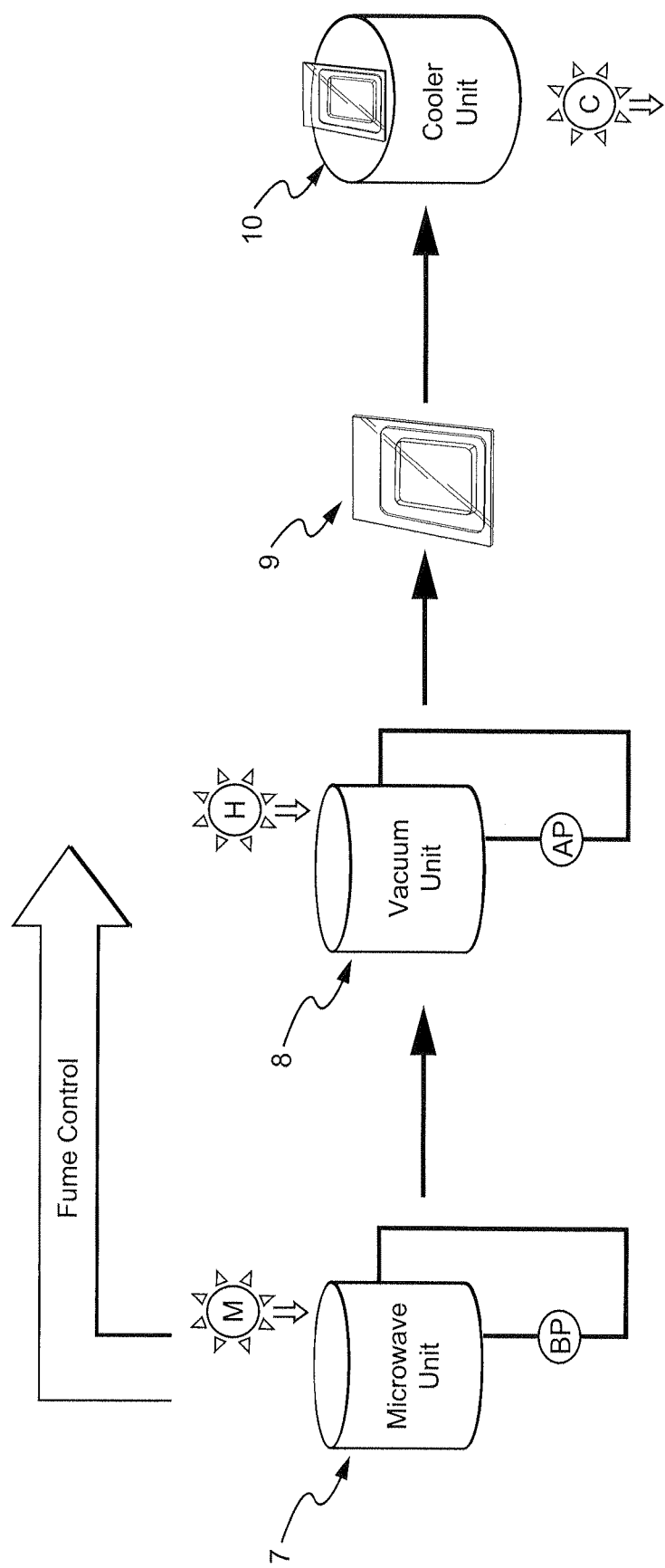
FIG. 3 is a schematic of another processing system without reservoirs.
Figure 4:
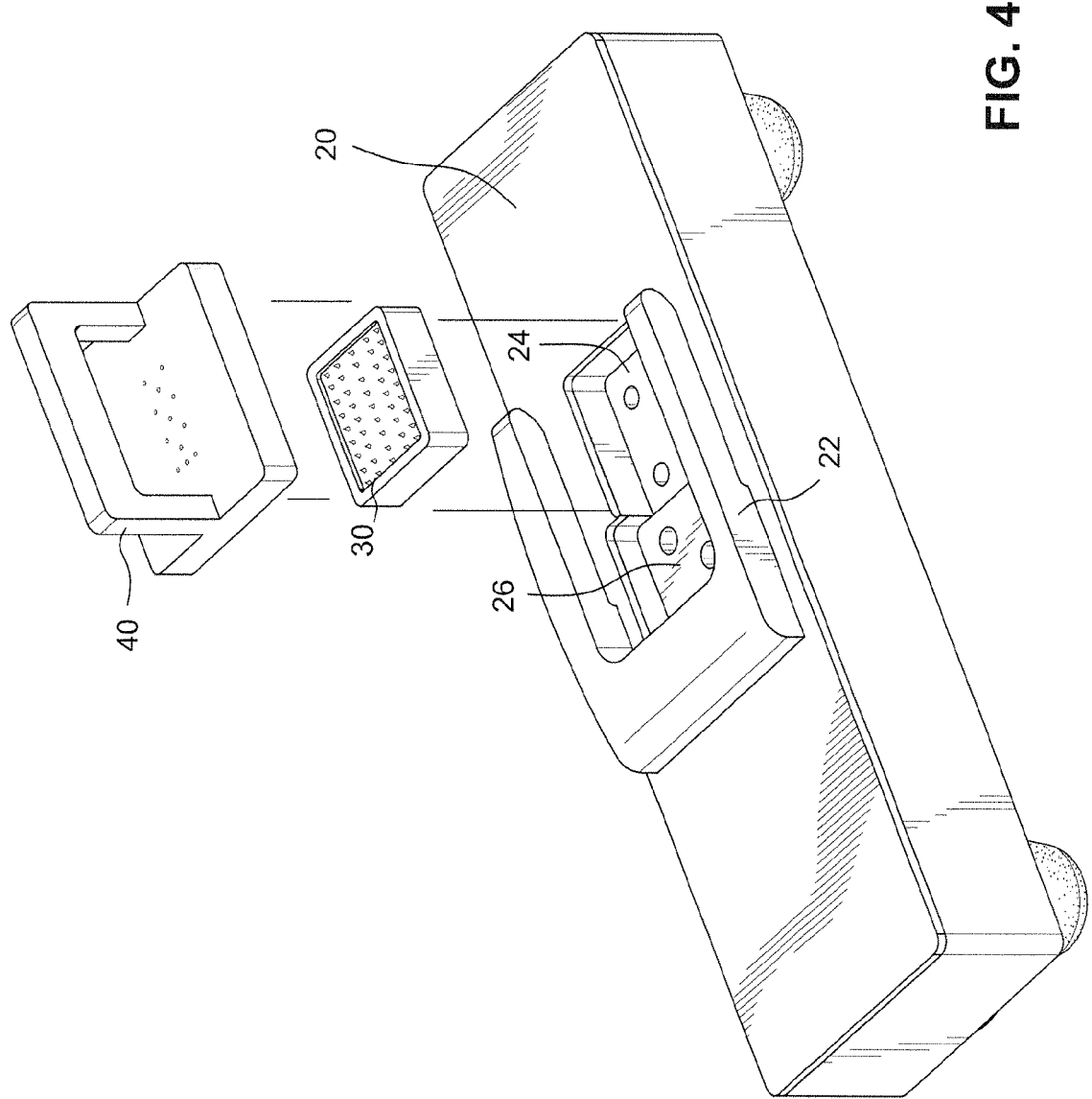
FIG. 4 is a perspective view of a system for grossing tissue.
Figure 5:
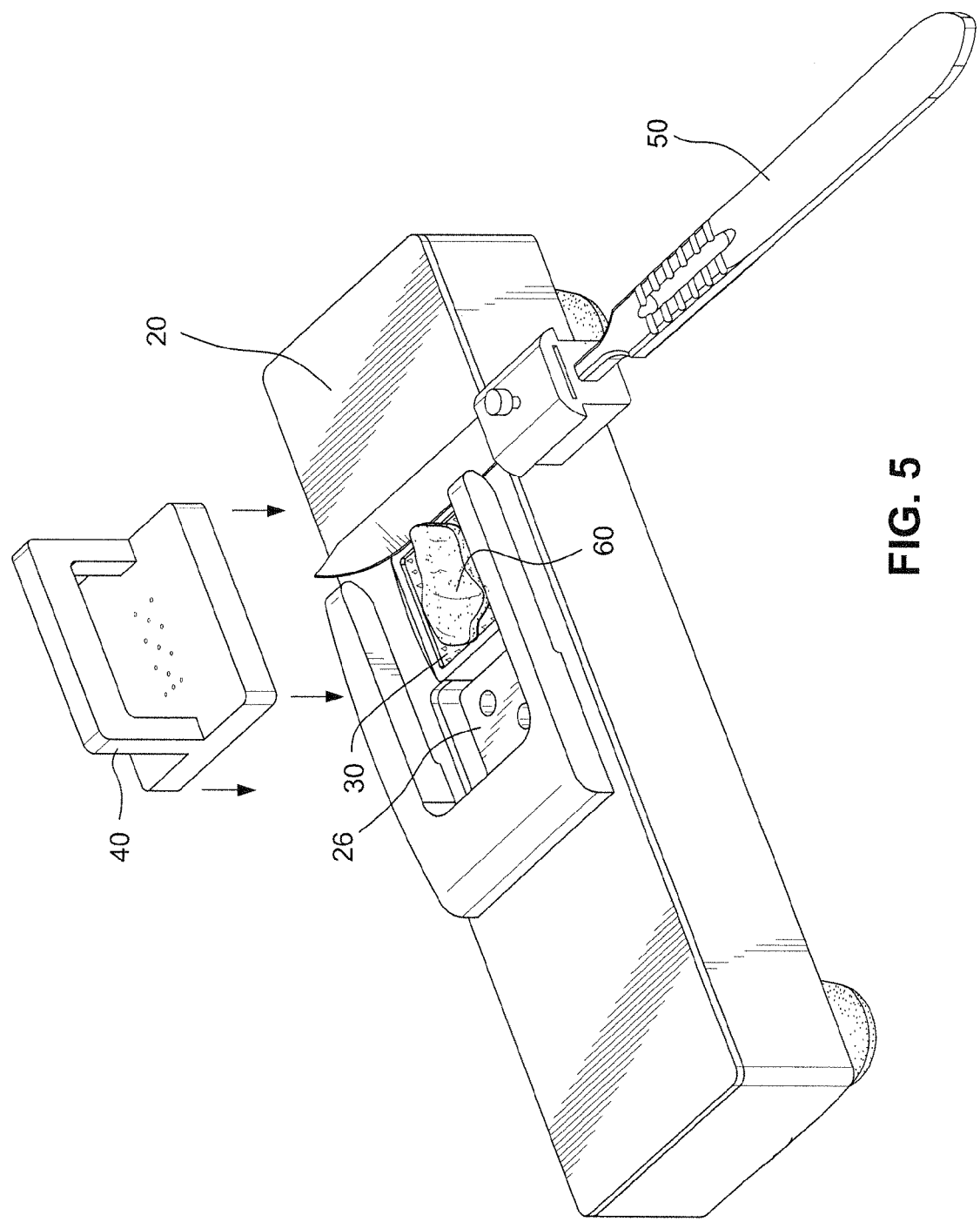
FIG. 5 is a perspective view of the grossing system of FIG. 4 prior to slicing of tissue.
Figure 6:
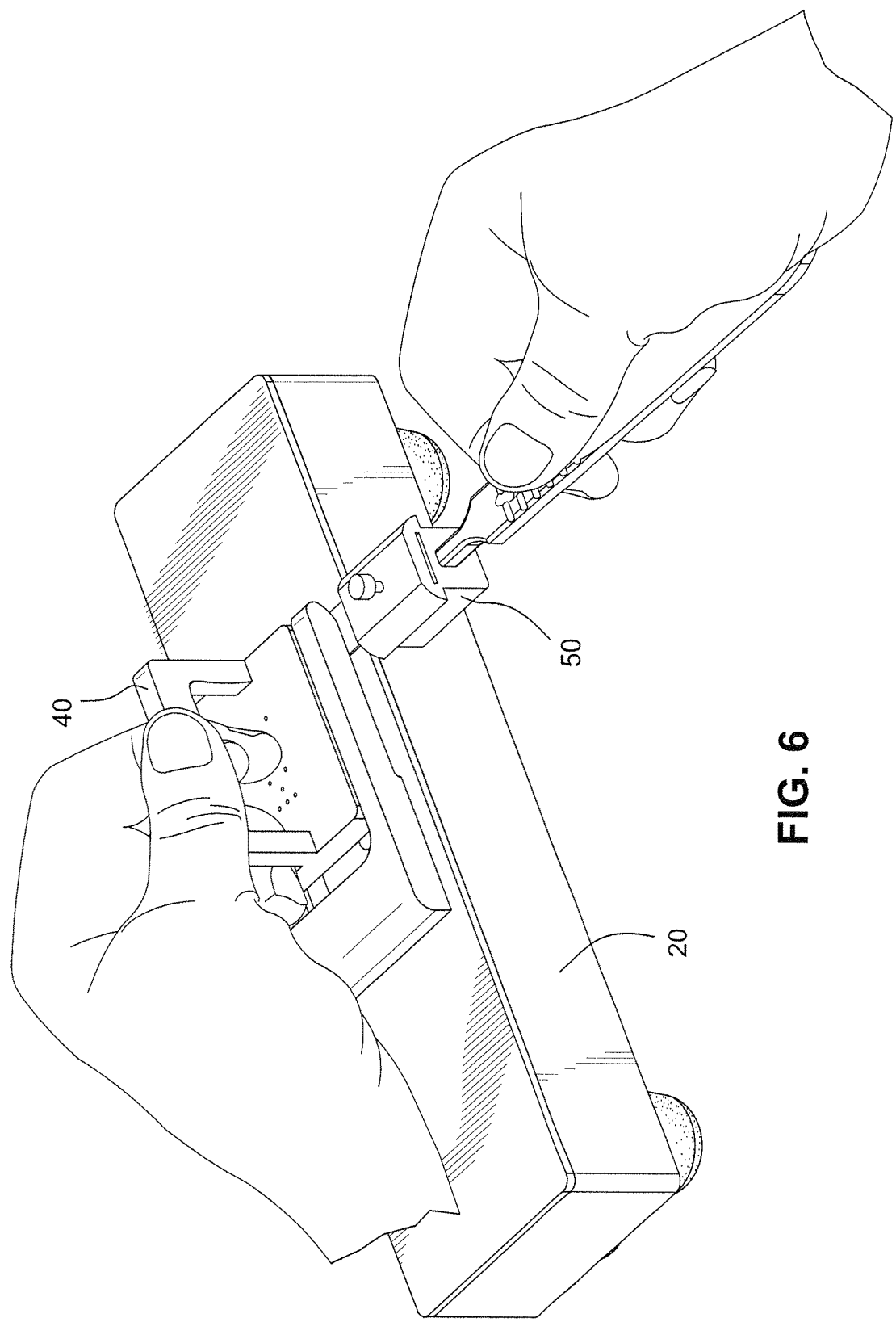
FIG. 6 is a perspective view of the grossing system of FIG. 4 during slicing of tissue, which is not seen in this view.
Figure 7:
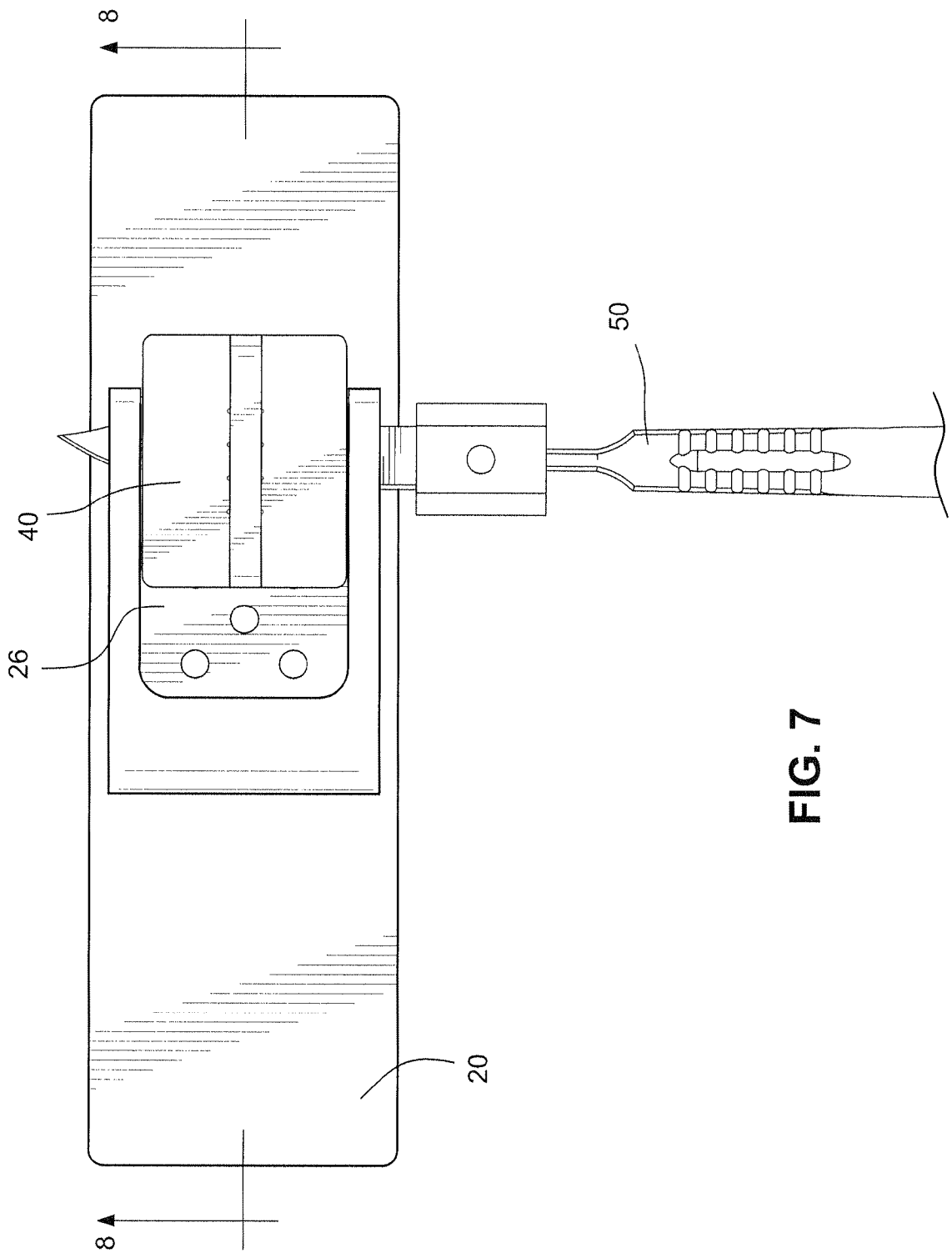
FIG. 7 is a top view of the grossing system of FIG. 4 during slicing of tissue, which is not seen in this view.
Figure 8:
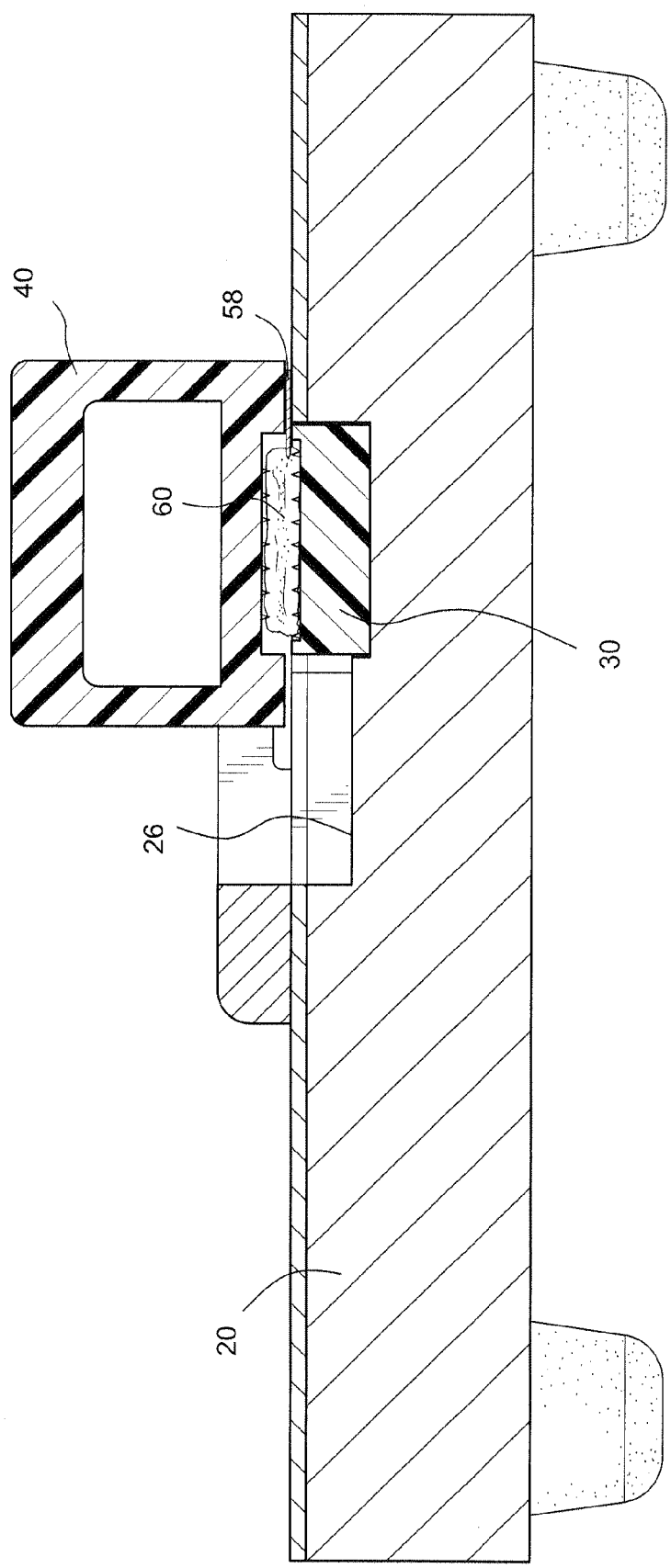
FIG. 8 is a cross-sectional view of the grossing system through line 8-8 of FIG. 7 showing tissue being held and sliced.
Figure 9:
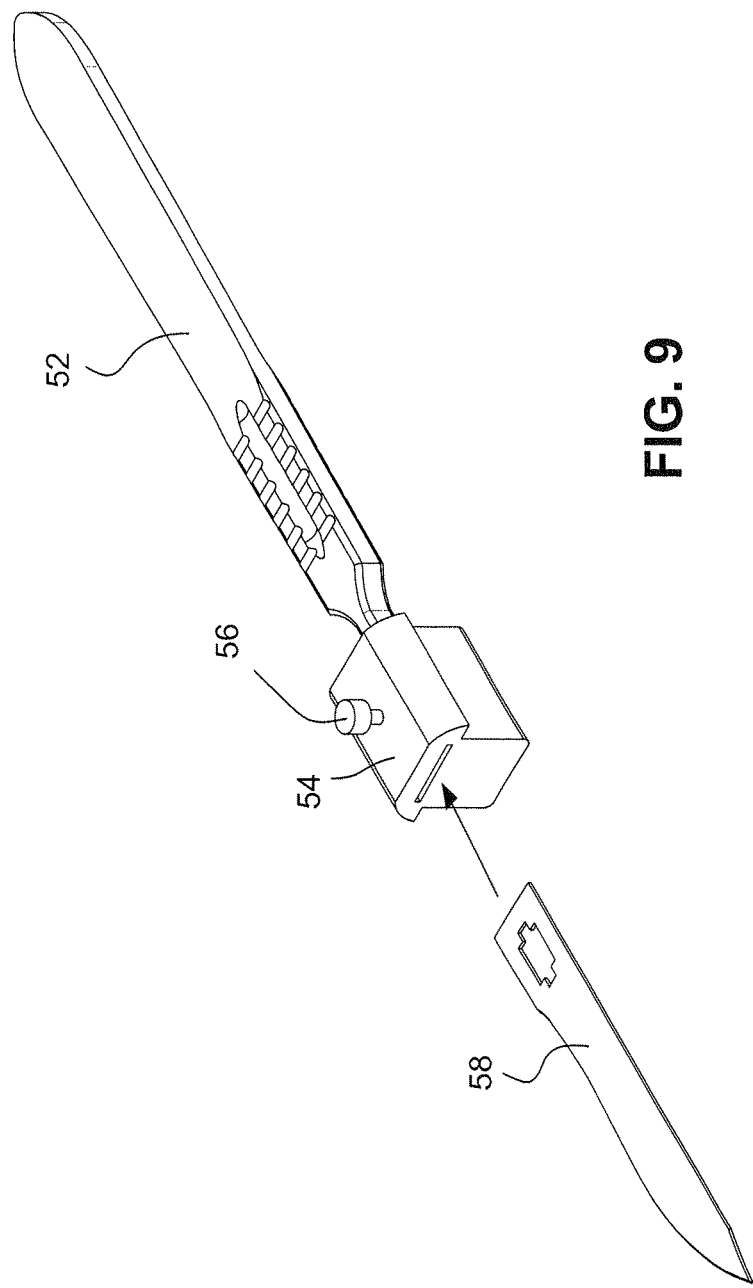
FIG. 9 is a perspective view of a grossing tool.

FIG. 3 illustrates an alternative embodiment, a version of the system similar to that described above with the exception that there are no reservoirs.

Figure 2:
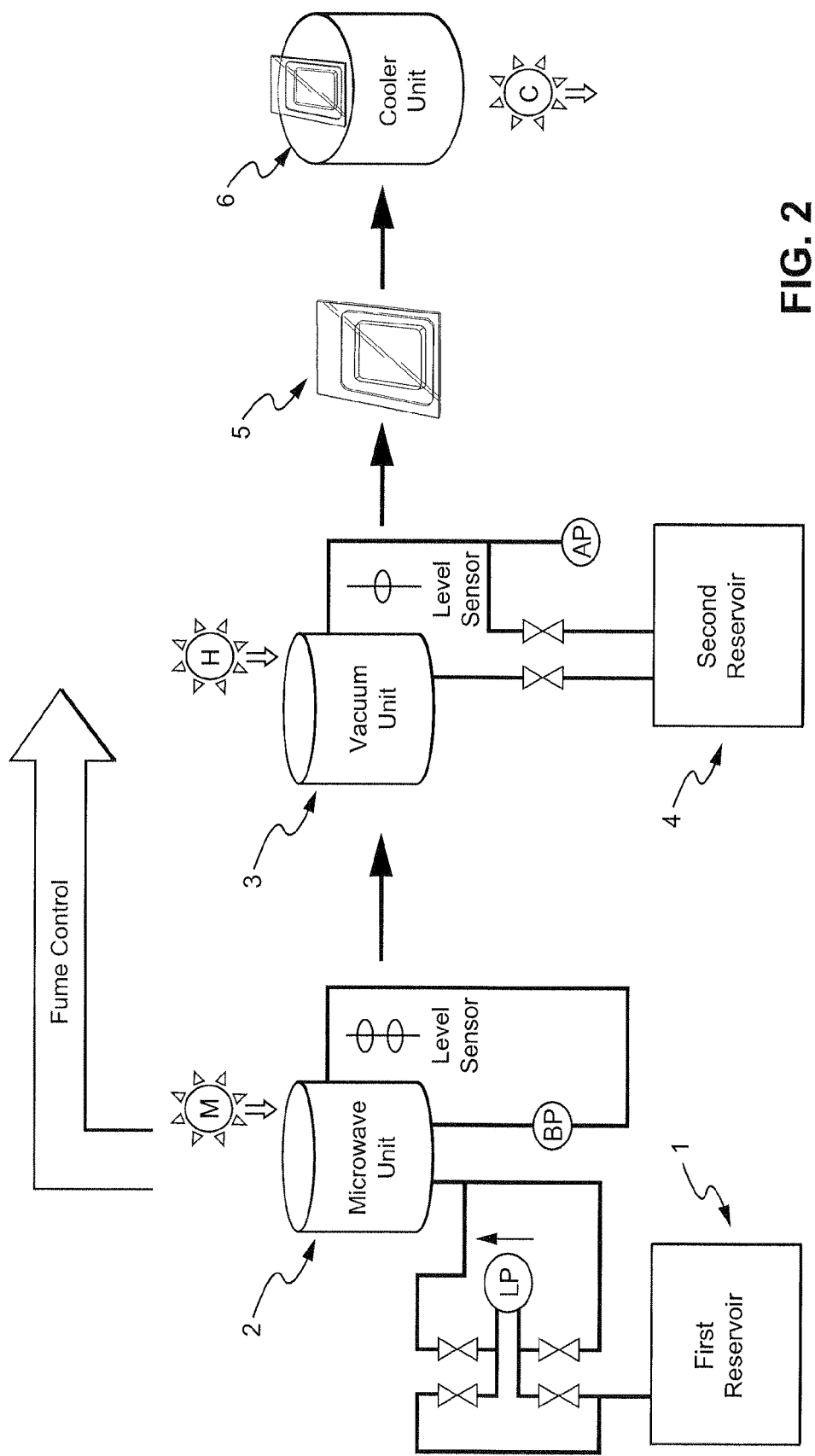
FIG. 2 is a schematic of a processing system having two reservoirs, which contain a chemical admixture that hardens a tissue specimen and a molten matrix that impregnates the hardened tissue specimen, respectively.

In both FIGS. 2 and 3, all units may be implemented in a single apparatus, they may be implemented in separate apparatuses, or the microwave and vacuum units may be implemented in one apparatus and the cooling unit in another.

Example 3

Grossing of Solid Tissue

Tissue grossing may be performed using another embodiment of the invention (shown in FIGS. 4 to 9) in the following manner. A grossing system is comprised of a base 20 that can be sanitized, a tissue support 30, and a tissue holder 40. Tissue support 30 and tissue holder 40 may be made from a resilient plastic material (e.g., acrylic). Each has a substantially flat abrasive surface (e.g., plurality of barbs, pins, or serrations having the approximate area of the fresh tissue); both abrasive surfaces contact tissue during grossing. The holder has a finger grip at top and an abrasive surface at bottom. Alternatively, the holder may be replaced by a finger to exert mild pressure on the solid tissue and push it against the support (not shown).

Tissue support 30 may be snuggly fitted by pushing with a finger into receiving well 24, such that top surfaces of the support 30 and the base 20 are substantially flush with each other and permit a blade to slice tissue when moved between the bottom of a blade guide 22 and the top of the base 20, wherein at least two blade guards of the guide 22 extend above the top surface of the base 20. The support 30 is comprised of a rim formed around a tissue-receiving depression having a depth of about 0.6 mm (e.g., from about 0.4 mm to about 0.8 mm, more preferably from about 0.5 mm to about 0.7). Prior to placing solid tissue in the tissue-receiving depression, it may be filled with a chemical admixture used for hardening. As an alternative to the support 30 being separate from the base 20, the former may be formed integrally with the latter such that there is no receiving well (not shown).

Solid tissue 60 may be sliced using a grossing tool 50. When the tissue 60 is placed in the tissue-receiving depression of support 30, the chemical admixture may contact the tissue 60, be displaced from the tissue-receiving depression, and spill into the adjacent well 26. Support 30 may be held in its receiving well 24 by friction, and may be manually removed by accessing through an adjacent well 26 and prying with a finger. Within the base 20, the bottom of well 26 may be set higher/lower than or even with the bottom of well 24. Grossing tool 50 slices the tissue 60 to a thickness of about 0.6 mm (e.g., from about 0.4 mm to about 0.8 mm, more preferably from about 0.5 mm to about 0.7) by moving the blade in at least two narrow slits, which are formed between the bottom of blade guide 22 and the top of base 20. Grossing solid tissue provides a tissue specimen having a substantially uniform thickness because the support's bottom surface and the base's top surface are substantially parallel to each other. Preferably, at least two blade guards of the guide 22 are at least separated by the width of the tissue-receiving depression and/or extend above the top surface of the base at least the length of the tissue-receiving depression.

A scalpel or grossing tool (FIG. 9) may be used to slice the solid tissue into one or more tissue specimens. The grossing tool comprises a handle 52, a holder 54, and a removable blade 58. The holder has two opposing ends: one end is permanently fixed to the handle and the opposite end has a gap formed therein. The blade is held in the gap by a screw 56, which travels in a direction perpendicular to the plane(s) of the blade and the handle. Putting the holder's mass between the handle's grip and the blade facilitates a horizontal slicing motion by proper weighting of the tool Example 4

Detection of Antigen in Tissue Sections

Tissue specimens are processed for 4-5 minutes in each of the microwave unit and the vacuum unit. Tissue specimens are each embedded in individual molds that contain an excess of paraffin. The tissue block may be solidified by assisted cooling. Wax sections are cut on a microtome to a thickness of 3 microns, placed in a water bath, and floated onto a glass slide. Wax in the tissue sections is melted on the slide, which is then dewaxed in a xylene bath. Sectioned tissue on the slide is rehydrated in a series of ethanol solutions of decreasing concentration for one minute each (two baths of absolute alcohol, two baths of 95% alcohol, and one bath of 90% alcohol) and rinsed by submerging in water for 2 minutes.

Endogenous peroxidase is blocked with a solution of 35 ml of 6% hydrogen peroxide ($H_2O_2$) and 140 ml of methanol, incubated for 15 minutes. Slides are rinsed by submerging in water for 2 minutes then phosphate buffered saline (PBS) for 2 minutes, and finally dried.

Slides are transferred to a humidity chamber and contacted with normal horse serum (NHS) for 10 minutes to block nonspecific binding sites. Excess normal horse serum is decanted from slides, and specific primary antibody is incubated for 30 minutes on the tissue section in a humidity chamber at room temperature. Slides are washed with a back-and-forth motion using a squeeze bottle containing PBS and submerging in a PBS bath for 2 minutes. Excess PBS is dried off each slide. Linking solution (also known as secondary antibody or biotinylated anti-rabbit or anti-mouse) is added to each tissue section and incubated for 25 minutes in a humidity chamber at room temperature. Rabbit, rat, and mouse secondary antibodies (e.g., anti-IgM, anti-IgG) may be obtained from Dako (Carpinteria, Calif.) and used at a dilution of about 1:600. Slides are washed using a squeeze bottle containing PBS and submerging in a PBS bath for 2 minutes. Excess PBS is dried off each slide.

Signal is developed according to the manufacturer's instructions (Vector Laboratories). Avidin-biotin complex (ABC) solution is added to the tissue section and incubated for 25 minutes in humidity chamber. Slides are flushed using a squeeze bottle containing PBS and submerging in a rack in a PBS bath for 2 minutes. The rack was submerged in a bath of diaminobenzidine (DAB) chromogen for 6 minutes, then submerged under running water to wash gently for 4 minutes. Tissue sections are counterstained with hematoxylin (staining time will depend on the age of the hematoxylin) from about 15 seconds to 90 seconds at room temperature. Slides are washed under running water for 3 minutes to remove excess counterstain, dehydrated in alcohol baths (about 10 seconds in each) from 85% alcohol to absolute alcohol, cleaned in xylene, and coverslipped.

In addition to common histochemical stains (e.g., H&E and trichrome), immunohistochemical staining of cytokeratin, ER, PR, Her2, E-cadherin, p63, PSA, EMA, HCA, RCA, AFP, HCG, CD10, CD30, CD31, CD45, CD68, and D2-40 antigens were performed.

Example 5

DNA Extraction from Processed Tissue Sections

Two wax sections (about 5-10 µm each) from a solid block of processed tissue are chopped using disposable blades. They are placed in a 1.5 ml microfuge tube, 800 µl xylene is added and mixed by vortexing, and 400 µl absolute ethanol is added and mixed by vortexing. The tube is centrifuged for 5 minutes in a microfuge, and the supernatant is decanted. To the pellet, 800 µl absolute ethanol is added and mixed by vortexing.

The supernatant is decanted after centrifugation, then 100 µl of a detergent and proteinase K solution (1% NP40 or Triton X-100, 2.4 µl of 2.5 mg/ml proteinase K) is added to the pellet and incubated at 55° C. for one hour. Proteinase K is inactivated by incubation at 95° C. for 10 minutes. The supernatant containing DNA is collected after centrifugation in a microfuge for 5 minutes. This material is ready for PCR. It should be precipitated and/or extracted further if Southern blotting is planned. More tissue sections might be required to obtain enough DNA for analysis that does not involve amplification. Fewer sections might be required for amplification.

Example 6

RNA Extraction from Processed Tissue Sections

Ten wax sections (about 5-10 µm each) from a solid block of processed tissue are chopped using disposable blades. They are placed in 50 ml Falcon tubes and dewaxed with 20 ml of xylene. The remaining tissue is washed twice with absolute alcohol for 30 minutes. The tissue is suspended at 0.5 gm/ml in a solution containing 4M guanidinium thiocyanate, 25 mM Na citrate pH 7.0, 0.5% N-laurylsarcosine, and 0.1 M of 2-mercaptoethanol. The solution is mixed by vortexing and DNA is sheared by passage through an 18 to 22 gauge syringe needle.

The RNA-containing solution is carefully layered on 2.8 ml of 5.7 M CsCl in 5 ml centrifuge tubes (Sorvall) and RNA is sedimented by centrifugation in an SW55Ti rotor at 35,000 rpm and 18° C. for 14 hours in a Beckman L8-53 ultracentrifuge. The top fraction is carefully removed to leave an RNA pellet at the bottom of the tube. The pellet is resuspended with ribonuclease-free water in an Eppendorf tube that is spun at 14,000 rpm for 10 minutes. The supernatant containing RNA is saved and the ultraviolet (UV) absorbance is measured: an extinction coefficient of 1 $OD_{280}$/cm is estimated to be the equivalent of about 40 µg/ml RNA and the $OD_{260}/OD_{280}$ ratio should be between about 1.8 and about 2.0. 18S and 28S rRNA bands are separated by denaturing gel electrophoresis. Indicative of good quality RNA purification are 18S and 28S rRNA bands present in the expected ratio and absence of degradation.

In stating a numerical range, it should be understood that all values within the range are also described (e.g., one to ten also includes every integer value between one and ten as well as all intermediate ranges such as two to ten, one to five, and three to eight). The term "about" may refer to the statistical uncertainty associated with a measurement or the variability in a numerical quantity which a person skilled in the art would understand does not affect operation of the invention or its patentability.

All modifications and substitutions that come within the meaning of the claims and the range of their legal equivalents are to be embraced within their scope. A claim using the transition "comprising" allows the inclusion of other elements to be within the scope of the claim; the invention is also described by such claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or inconsequential activities which are ordinarily associated with the invention) instead of the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

I claim:

1. A system for processing of a specimen from a solid tissue, comprising:
   (a) a hardening module to harden the specimen, comprised of (i) a first chamber having an interior shaped as a whispering gallery, (ii) a first lid that isolates the first chamber when closed, is opaque to microwave radiation, and accesses the first chamber when open, (iii) a first gasket retaining chemical fumes and evaporation within the interior of the first chamber, and (iv) a radiation source transmitting microwave energy to the interior of the first chamber; wherein the specimen is contacted with a chemical admixture in the whispering gallery;
   (b) an impregnating module to impregnate the specimen that was hardened, comprised of (i) a second chamber having an interior capable of providing a reduced pressure relative to the exterior, (ii) a second lid that isolates the second chamber when closed and accesses the second chamber when open, (iii) a gasket maintaining a pressure differential between the interior and the exterior of the second chamber, (iv) a pump at least decreasing pressure within the interior of the second chamber below 1 bar, and (v) a heater conducting thermal energy to the interior of the second chamber; wherein the hardened specimen is contacted with a molten matrix in the chamber; and
   (c) an embedding module to solidify a block containing the specimen that was hardened and impregnated, comprised of a cooler conducting thermal energy from the block.

2. The system of claim 1, wherein the hardening module is further comprised of a first agitator, which may be an aerator, within the whispering gallery to promote solution exchange between the chemical admixture and the specimen.

3. The system of claim 1, wherein the impregnating module is further comprised of a second agitator, which may be a valve cycling the pressure, within the chamber to promote solution exchange between the molten matrix and the specimen.

4. The system of claim 1, wherein the specimen is substantially hardened by the chemical admixture, the microwave energy, or both.

5. The system of claim 1, wherein the specimen is substantially impregnated then embedded in a block using the same matrix.

6. The system of claim 1, wherein the radiation source maintains chemical admixture in the first chamber at a temperature of above about 45° C., above about 50° C., above about 55° C., above about 60° C., below about 60° C., below about 65° C., below about 70° C., below about 75° C., or at a temperature in any range therebetween.

7. The system of claim 1, wherein pressure in the chamber is above about 0.001 bar, above about 0.01 bar, above about 0.1 bar, below about 0.2 bar, below about 0.3 bar, below about 0.4 bar, below about 0.5 bar, below 1 bar, or at a pressure in any range therebetween.

8. The system of claim 1, wherein the heater maintains molten matrix in the second chamber at a temperature of above about 55° C., above about 60° C., above about 65° C., below about 65° C., below about 70° C., below about 75° C., below about 80° C., below about 85° C., or at a temperature in any range therebetween.

9. The system of claim 1, wherein the cooler is maintained at a temperature of below about −50° C., below about −25° C., below about 0° C., below about +5° C., above about −200° C., above about −100° C., above about −50° C., above about −25° C., or at a temperature in any range therebetween.

10. The system of claim 1 further comprising a conveyance connecting at least hardening and impregnating modules, impregnating and embedding modules, or hardening, impregnating and embedding modules.

11. The system of claim 10, wherein the conveyance comprises a track or an armature connecting successive modules.

12. The system of claim 10 further comprising a plurality of carriers having perforations that allow solution exchange between specimen and either admixture or matrix, wherein each specimen is enclosed within one of the plurality of carriers and each carrier is reversibly attached to the conveyance so batches of carriers may be continuously processed.

13. The system of claim 10 further comprising a starting module at which a tissue specimen enters the system, then is conveyed to the hardening module.

14. The system of claim 10 further comprising an ending module to which an embedded specimen is conveyed from the embedding module, then waits to be collected.

15. A method for processing of a specimen from a solid tissue, comprising:
   (a) hardening the specimen in a whispering gallery, wherein the specimen is contacted with a chemical admixture and microwave energy;
   (b) impregnating the specimen under vacuum, wherein the specimen is contacted with a molten matrix and thermal energy;
   (c) embedding the specimen in a block and solidifying the block, wherein the solid block may be sectioned for histologic examination intraoperatively; and
   (d) cooling the block by exposing the block to a cooling source.

16. The method according to claim 15 further comprising grossing fresh tissue outside a subject's body to provide the specimen, wherein the specimen is initially hardened in a chemical admixture, which may be the same or different from the chemical admixture used for processing, during grossing.

17. The method according to claim 15, wherein the specimen has a thickness less than about 1 mm, less than about 0.8 mm, or less than about 0.6 mm.

18. The method according to claim 15, wherein the chemical admixture is a non-aqueous solution comprising (i) at least one ketone, which may be acetone, and (ii) at least one oil, which may be mineral oil or pine oil.

19. The method according to claim 15, wherein the chemical admixture is further comprised of at least one surfactant, which may be dimethyl sulfoxide.

20. The method according to claim 15, wherein the matrix is comprised of at least one paraffin wax.

21. The method according to claim 15, wherein the specimen is substantially hardened by the chemical admixture, the microwave energy, or both.

22. The method according to claim 15, wherein the specimen is substantially impregnated then embedded in a block using the same matrix.

23. The method according to claim 15, wherein the chemical admixture is at a temperature of above about 45° C., above about 50° C., above about 55° C., above about 60° C., below about 60° C., below about 65° C., below about 70° C., below about 75° C., or at a temperature in any range therebetween.

24. The method according to claim 15, wherein the vacuum is above about 0.001 bar, above about 0.01 bar, above about 0.1 bar, above about 0.5 bar, above about 0.6 bar, above about 0.7 bar, below about 0.2 bar, below about 0.3 bar, below about 0.4 bar, below about 0.5 bar, below about 0.6 bar, below about 0.7 bar, below about 0.8 bar, below about 0.9 bar, or below about 1 bar, or at a pressure in any range therebetween.

25. The method according to claim 15, wherein the molten matrix is at a temperature of above about 55° C., above about 60° C., above about 65° C., below about 65° C., below about 70° C., below about 75° C., below about 80° C., below about 85° C., or at a temperature in any range therebetween.

26. The method according to claim 15, wherein the block is solidified by cooling at a temperature of below about −50° C., below about −25° C., below about 0° C., below about +5° C., above about −200° C., above about −100° C., above about −50° C., above about −25° C., or at a temperature in any range therebetween.

27. The method according to claim 15, wherein the specimen is at least partially or completely processed manually.

28. The method according to claim 15, wherein the specimen is at least partially or completely processed automatically.

29. The method according to claim 15, wherein the specimen is substantially hardened after being contacted with the chemical admixture and the microwave energy for less than about 10 minutes, less than about 8 minutes, less than about 6 minutes, more than about 2 minutes, more than about 4 minutes, more than about 6 minutes, or for a time in any range therebetween.

30. The method according to claim 15, wherein the specimen is substantially impregnated after being contacted with the molten matrix and the thermal energy for less than about 10 minutes, less than about 8 minutes, less than about 6 minutes, more than about 2 minutes, more than about 4 minutes, more than about 6 minutes, or for a time in any range therebetween.

31. The method according to claim 15, wherein the block can be sectioned after being solidified for less than about 5 minutes, less than about 4 minutes, less than about 3 minutes, more than about 1 minute, more than about 2 minutes, more than about 3 minutes, or for a time in any range therebetween.

* * * * *